United States Patent [19]

McNeil et al.

[11] 4,135,883
[45] Jan. 23, 1979

[54] BLOOD ANALYZER SYSTEM

[75] Inventors: Mark D. McNeil, Irvine; Robert H. Goldstein, Tustin, both of Calif.; Robert M. Stahl; Sandra L. Piepho, both of Indianapolis, Ind.

[73] Assignee: Bio-Dynamics Inc., Indianapolis, Ind.

[21] Appl. No.: 828,522

[22] Filed: Aug. 29, 1977

[51] Int. Cl.² .......................................... G01N 33/16
[52] U.S. Cl. .................................... 422/72; 233/26; 422/55
[58] Field of Search ............... 23/253 R, 259, 230 R; 233/26

[56] References Cited

U.S. PATENT DOCUMENTS

| | | | |
|---|---|---|---|
| 2,663,461 | 12/1953 | Brown | 222/107 |
| 2,861,572 | 11/1958 | Hind et al. | 128/233 |
| 2,984,146 | 5/1961 | Kwart et al. | 88/14 |
| 3,026,764 | 3/1962 | Allen et al. | 88/14 |
| 3,050,239 | 8/1962 | Williams, Jr. | 233/24 |
| 3,344,702 | 10/1967 | Wood et al. | 88/14 |
| 3,415,627 | 10/1968 | Rait | 23/253 R |
| 3,452,924 | 7/1969 | Schlutz | 233/14 |
| 3,477,822 | 11/1969 | Hamilton | 23/253 R |
| 3,481,712 | 12/1969 | Bernstein et al. | 23/259 X |
| 3,497,320 | 2/1970 | Blackburn et al. | 23/230 R |
| 3,532,470 | 10/1970 | Rochte | 23/253 R |
| 3,540,858 | 11/1970 | Rochte et al. | 23/253 R |
| 3,713,775 | 1/1973 | Schmitz | 23/253 R |
| 3,759,666 | 9/1973 | Hill, Jr. | 23/253 X |
| 3,856,470 | 12/1974 | Cullis et al. | 23/259 X |

*Primary Examiner*—R.E. Serwin
*Attorney, Agent, or Firm*—Woodard, Weikart, Emhardt & Naughton

[57] ABSTRACT

Medical testing apparatus including a microprocessor controlled centrifuge having a group of cuvettes therein. The apparatus also includes a microdiluter apparatus with a pair of pumps therein of differing diluting capability. The cuvettes have hollow main bodies produced from transparent material to allow analysis of the specimen within the cuvettes by a series of spectrophotometers adapted to read the cuvettes while they are rotating within the centrifuge. Bags of reagent are received within the cuvettes and are designed to burst upon reaching a given level of centrifugal force allowing the reagent to flow from the bags into a test chamber within the cuvette main body. Projections are provided on the cuvettes to control the orientation of the cuvettes when inserted into the microdiluter apparatus. A tab is provided on each cuvette in proper orientation to actuate the appropriate microdiluter pump for the test the cuvette is intended for. The cuvette projections also are coded with a binary code to produce a signal which indicates to the test apparatus which test is being carried out in the cuvette. The apparatus also includes means for receiving the signal from the code reader and from the spectrophotometer and for printing out the test results appropriate for the coding.

25 Claims, 23 Drawing Figures

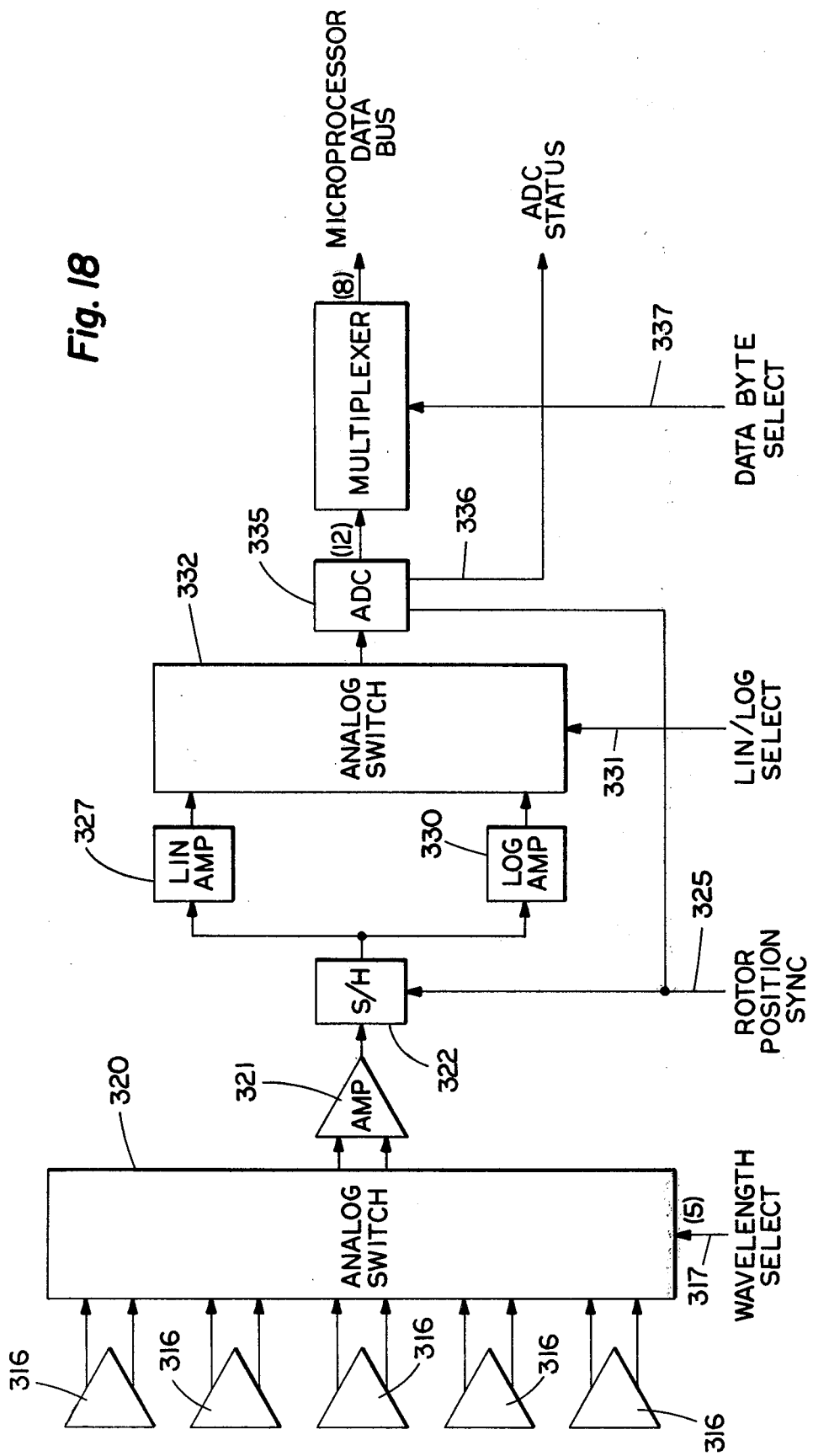

BLOOD ANALYZER SYSTEM

BACKGROUND OF THE INVENTION

1. Field of the Invention:

This invention relates to chemical testing apparatus.

2. Description of the Prior Art:

There are available in the prior art various devices and procedures for facilitating the running of medical tests. Certain devices and procedures marketed by applicants' assignee pre-package some of the reagents for a given test in the test cuvette and precalibrate the meter used in the test. Other devices separate the test specimens by bubbles and move the test specimens along a tube whereby sequential testing is accomplished in a completely automatic fashion. These devices are subject to certain disadvantages. For example, the use of a single cuvette in a colorimeter is a slow process because only one cuvette can be tested in the colorimeter at a time. Also, the steps involved in running the test depend in some degree on the skill and knowledge of the operator. For example, the operator may or may not properly mix the reagents and the specimen. Also, the above mentioned "bubble" separation test procedure is a very expensive device which is only appropriate in the larger laboratories and hospitals where substantial numbers of tests are carried out in a given period of time.

Certain other prior art is disclosed in the following articles: "Analytical Techniques for Cell Fractions" from *Analytical Biochemistry* 28, pp. 545–562 (1969); "Computer Interfaced Fast Analyzers" from *Science*, Oct. 17, 1969, Volume 166, Number 3903; and "Analytical Techniques for Cell Fractions" from *Analytical Biochemistry* 23, pp. 207–218 (1968) all of which relate to the simultaneous use of a centrifuge and a photometer. Other prior art is disclosed in the following U.S. Pat. Nos.:

| | | |
|---|---|---|
| 2,663,461 | Brown | Dec. 22, 1953 |
| 2,861,572 | Hinde et al. | Nov. 25, 1958 |
| 2,984,146 | Kwart et al. | May 16, 1961 |
| 3,026,764 | Allen et al. | March 27, 1962 |
| 3,050,239 | Williams, Jr. | Aug. 21, 1962 |
| 3,344,702 | Wood et al. | Oct. 3, 1967 |
| 3,415,627 | Rait | Dec. 10, 1968 |
| 3,452,924 | Schultz | July 1, 1969 |
| 3,477,822 | Hamilton | Nov. 11, 1969 |
| 3,481,712 | Bernstein et al. | Dec. 2, 1969 |
| 3,497,320 | Blackburn et al. | Feb. 24, 1970 |
| 3,713,775 | Schmitz | Jan. 30, 1973 |

SUMMARY OF THE INVENTION

One embodiment of the chemical test apparatus of the present invention might include a centrifuge having a rotor. A cuvette having a test chamber and coding thereon is mounted on the rotor of the centrifuge. A spectrophotometer is mounted on the centrifuge and is adapted to read the test chamber of the cuvette as the rotor of the centrifuge rotates. There is also provided means for reading the coding on the cuvette and means for receiving this signal from the code reader and from the spectrophotometer and for displaying the result appropriate for the coding.

Objects of the present invention are to provide improved medical test apparatus, to provide medical test apparatus including means for proper specimen dilution, to provide medical test apparatus capable of running any desired balance of end point or kinetic chemistries, and to provide medical test apparatus with an improved control system.

BRIEF DESCRIPTION OF THE DRAWINGS

FIG. 18 is a schematic drawing of the optical data acquisition section of FIG. 16.

FIG. 19 is a schematic drawing of the cuvette code reader and rotor position circuit of FIG. 16.

DESCRIPTION OF THE PREFERRED EMBODIMENT

Figure 1:
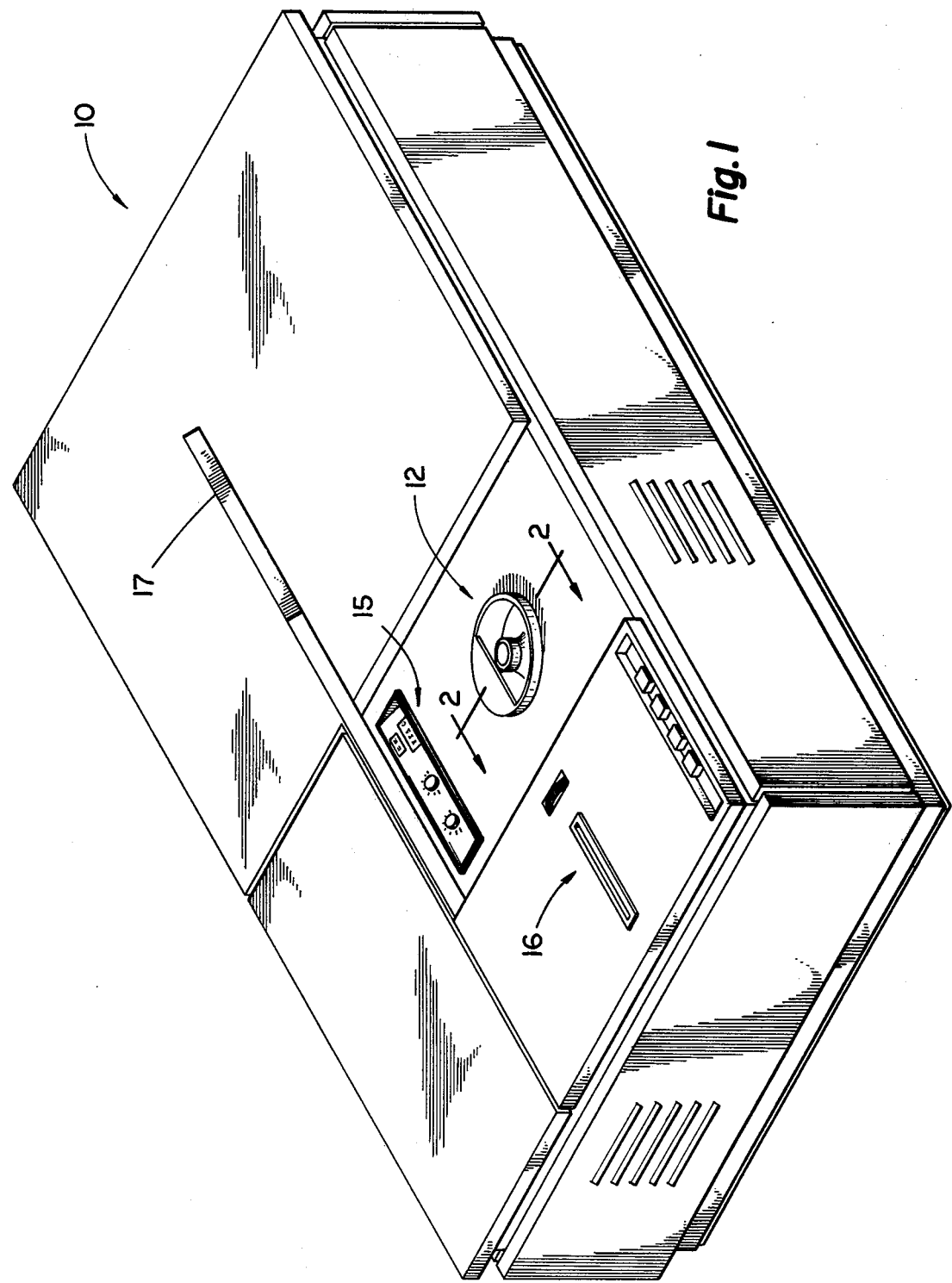
FIG. 1 is a perspective view of a combined centrifugespectrophotometer incubator apparatus embodying the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 13:
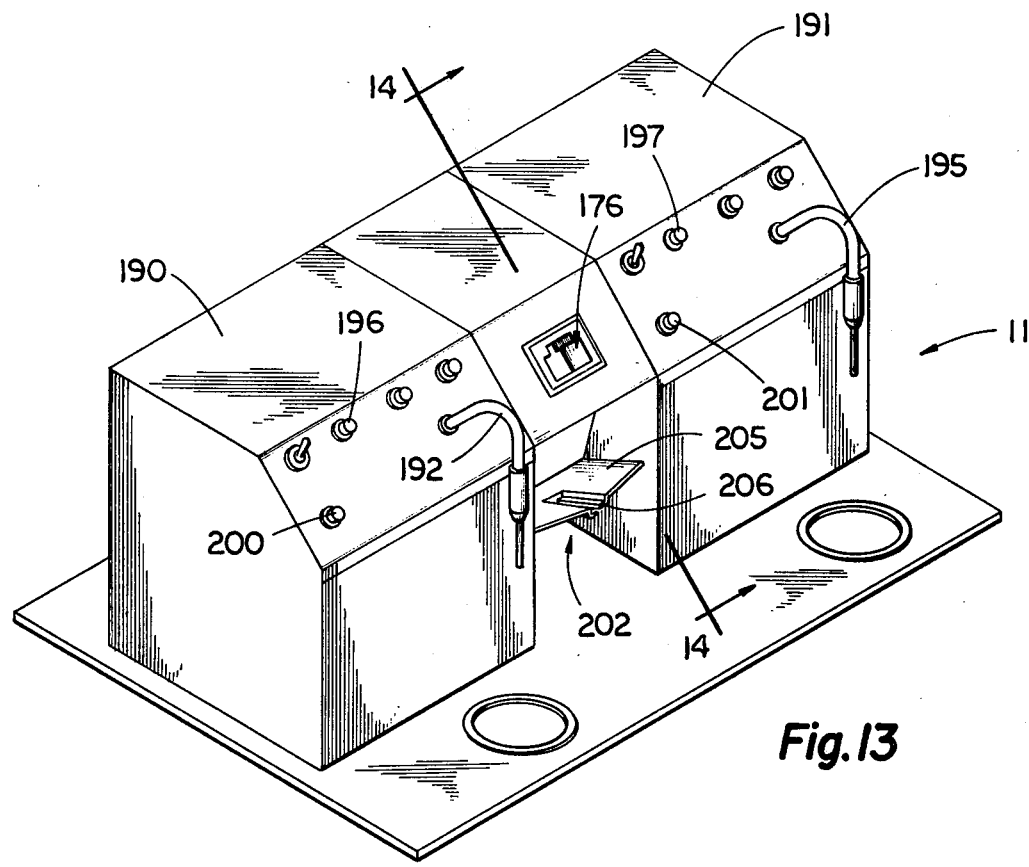
FIG. 13 is a perspective view of a microdilution apparatus embodying the present invention.
Figure 14:
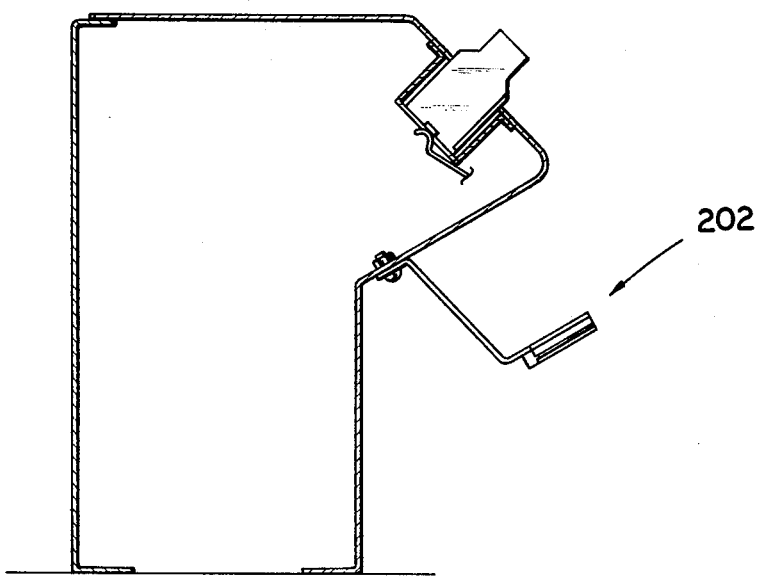
FIG. 14 is a section taken along the line 14—14 of FIG. 13.
Figure 15:
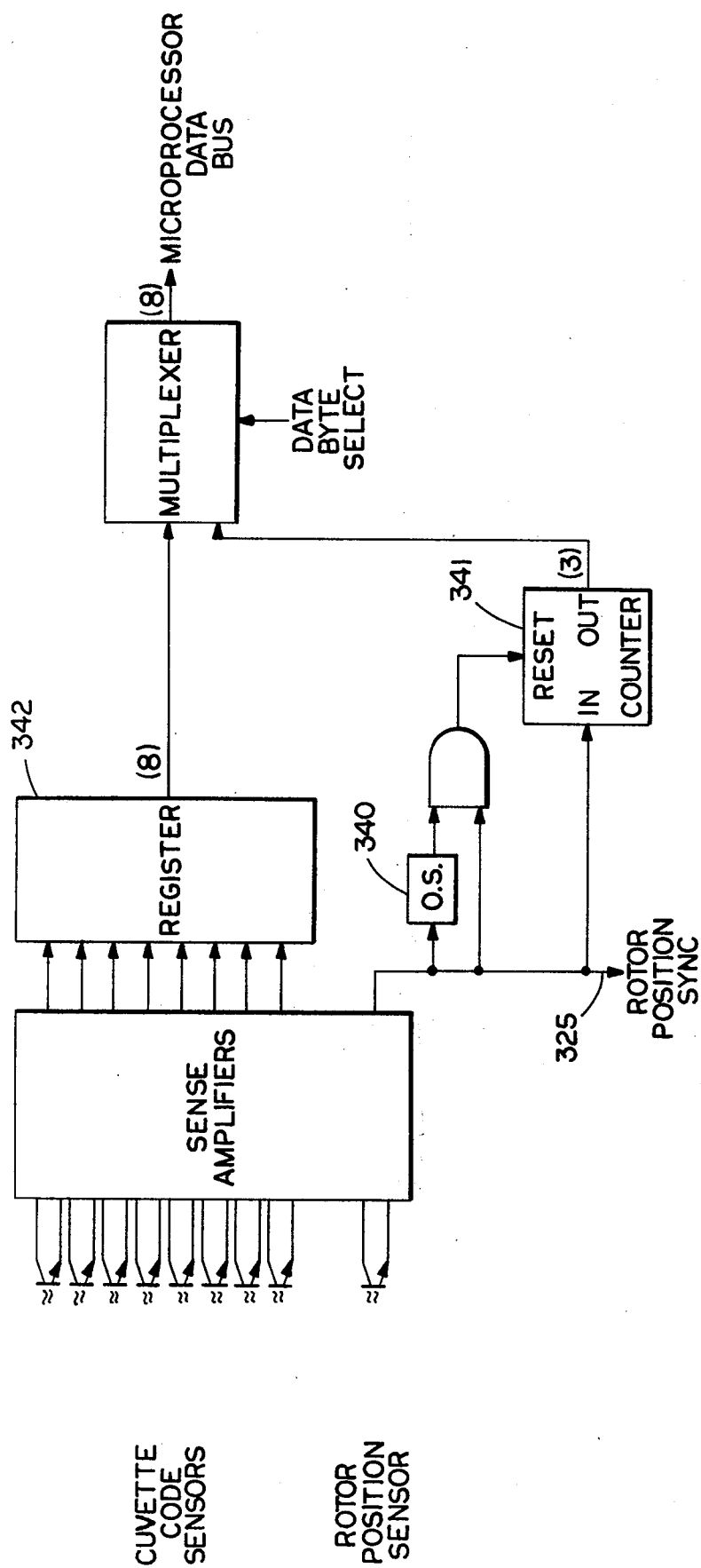
FIG. 15 is an enlarged sectional view of a portion of the structure illustrated in FIG. 14 showing it being used to remove the plug from a cuvette.

Referring to FIGS. 1-4, there is illustrated a blood analyzer system apparatus which includes the combined centrifuge-spectrophotometer-incubator apparatus 10 of FIG. 1 and the microdilution apparatus 11 of FIGS. 13-15. The apparatus 10 includes a centrifuge 12 shown in section in FIG. 2. As shown in FIG. 1, the apparatus 10 includes a control panel 15, a printer 16 and a cover 17 for the centrifuge shown in detail in FIG. 2. The centrifuge includes a motor 20 fixedly mounted to the rotor housing base plate 21 by motor mounts 22. A rotor 25 is fixed to the shaft 27 of the motor 20 by rotor retainer 26. The base plate 21 is mounted to the frame 30 of the apparatus 10 by the support rods 31 and isolation mounts 32.

A rotor housing 35 includes the base plate 21 and an upper plate 37 which are fixed together and provide the housing within which the rotor 25 turns. Mounted to the housing upper plate 37 is a code lamp housing 40 which contains a code lamp adapted to provide light to eight sensors 41 mounted on the base plate 21 of the rotor housing 35. The rotor 25 has recesses 42 within which cuvettes can be received for centrifuging, code reading and transmittance or absorbance reading. In the present embodiment of the invention there are eight such numbered recesses in the rotor 25 as shown in FIG. 5, although this number could vary.

Figure 3:
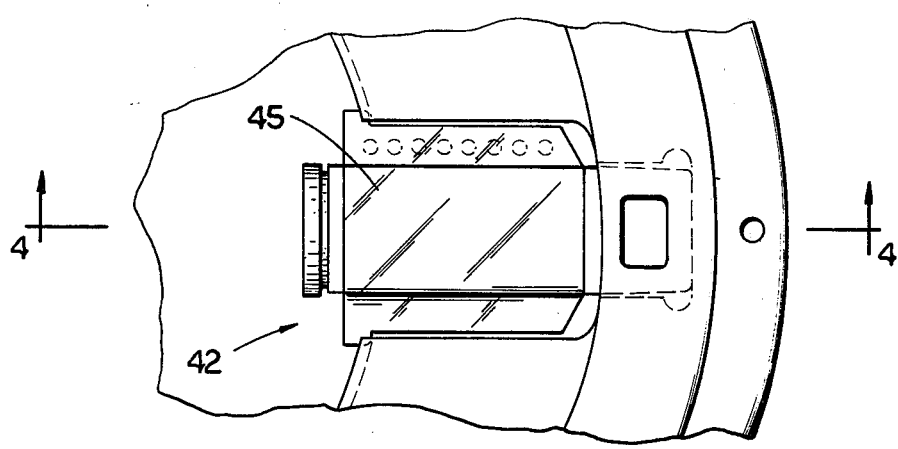
FIG. 3 is an enlarged fragmentary top plan view of a rotor forming a part of the structure of FIGS. 1 and 2.
Figure 2:
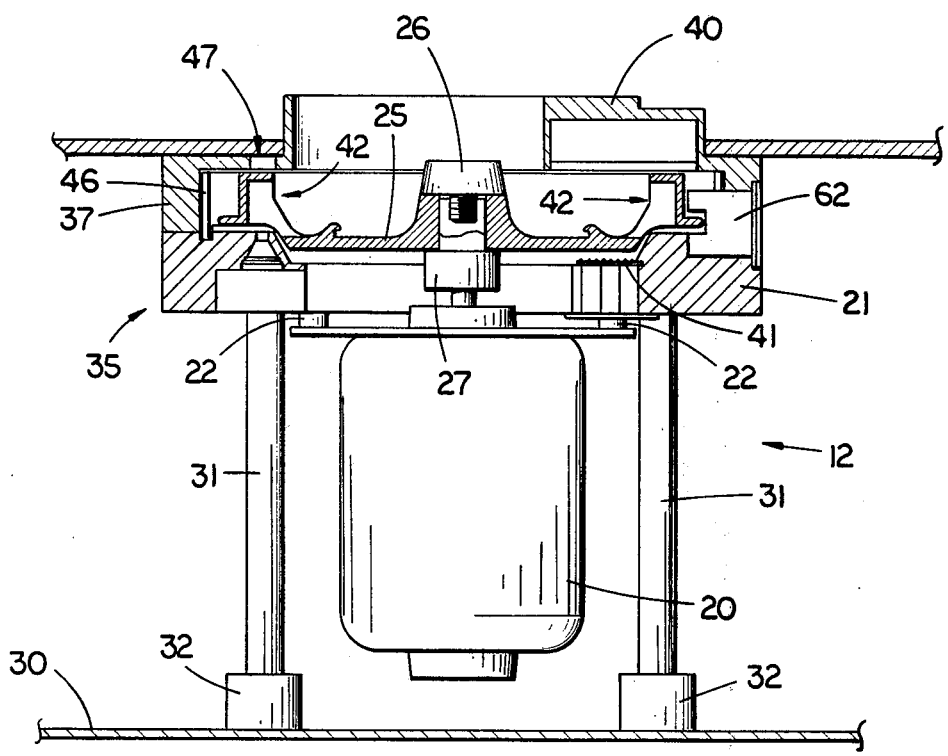
FIG. 2 is a vertical section taken on the line 2—2 of FIG. 1.
Figure 4:
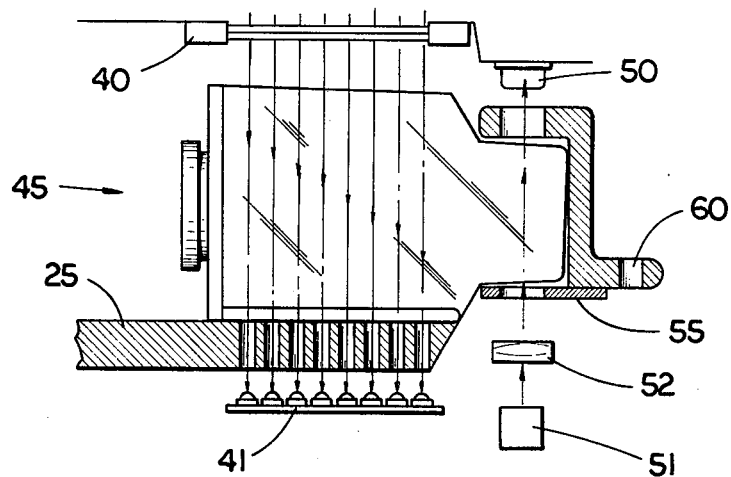
FIG. 4 is a somewhat schematic vertical section taken generally along the line 4—4 of FIG. 3 in the direction of the arrows and also having associated functional structure.

In FIG. 3 an enlarged plan view of the rotor is shown with a cuvette 45 mounted in one of the recesses 42 thereon. FIGS. 5 and 6 are mechanical drawings of the rotor 25. The rotor housing 35 has a heater strip 46 therein which consists of nichrome wire silicon pad heating elements. The heater strip 46 is used to maintain the temperature of the rotor and the cuvettes carried thereby at 37° C. At five locations in the rotor housing 35 there are spectrophotometer assemblies 47 for five different wave lengths. These spectrophotometer assemblies are located at 45° intervals around the rotor and are each physically located to read the transmittance or absorbance of all of the cuvettes in the rotor as the cuvettes pass through the rotor. FIG. 4 shows a representative one of the spectrophotometer assemblies as consisting of a sensor 50, a light source 51, a focusing lens 52 and a filter 55 adapted to pass light of only a single wave length. The frequencies of the different filters are 340, 405, 540, 580 and 610 manometers which are particularly adapted for the various tests which can be run with the present apparatus.

Figure 5:
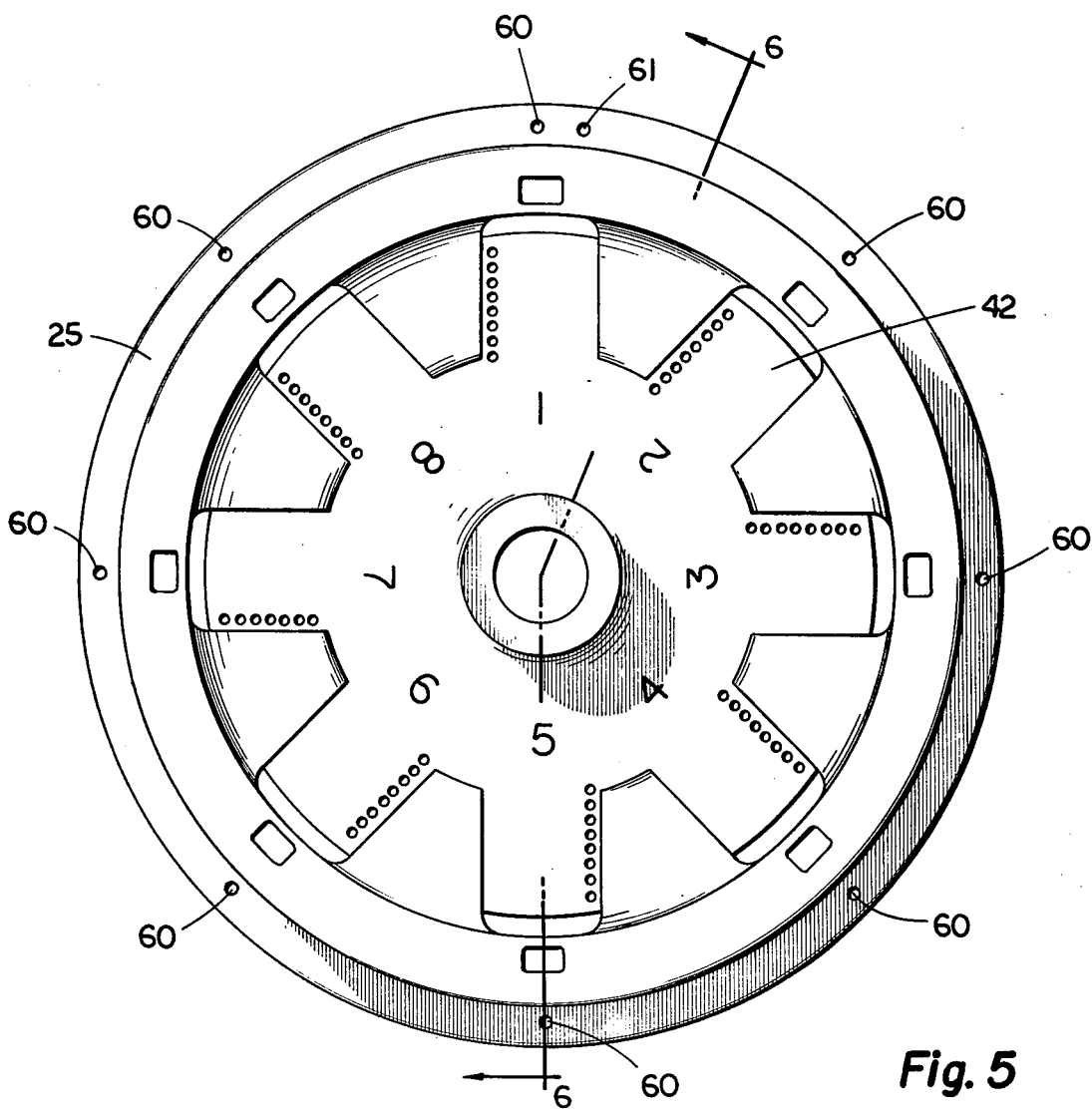
FIG. 5 is a plan view of the rotor.
Figure 6:
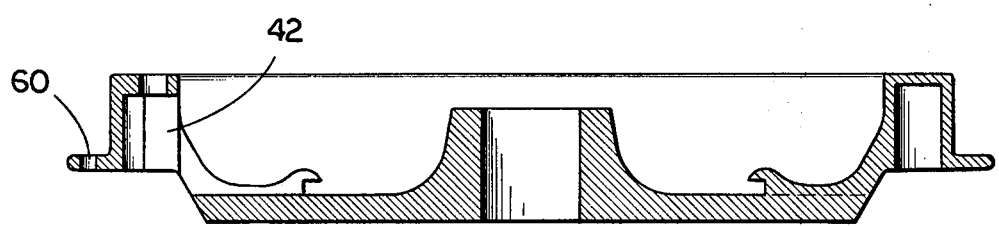
FIG. 6 is a vertical section taken along the line 6—6 of FIG. 5 in the direction of the arrows.

The rotor 25 as shown in FIG. 5 has holes 60 located at each of the numbered recesses 42. The first numbered recess "NO 1" has an additional hole 61 located just adjacent the hole 60 for the recess "NO 1". The holes 60 and 61 are sensed as the rotor rotates by a light and phototransistor assembly 62 mounted on the rotor housing 35.

Figure 7:
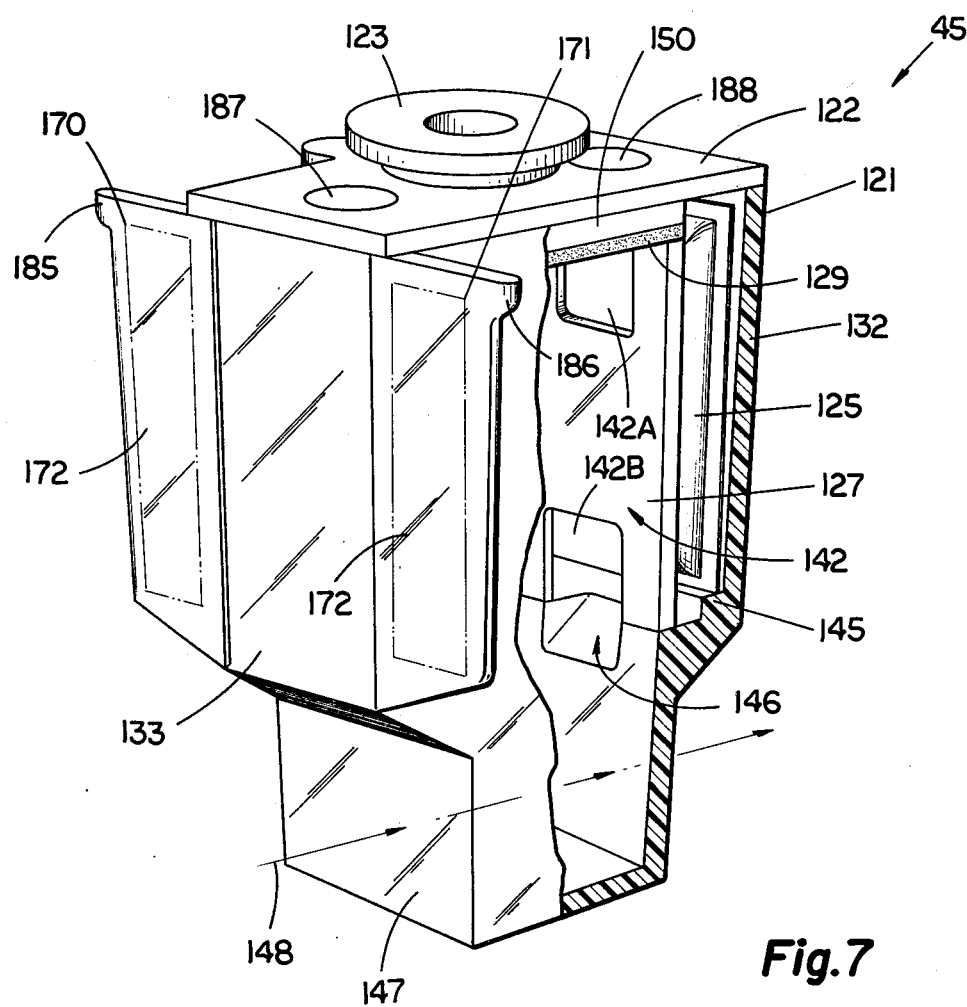
FIG. 7 is a fragmentary perspective view of a cuvette of the present invention.

Referring to FIG. 7, cuvette 45 is shown in greater detail. The cuvette is used to hold the liquid specimen being analyzed by one of spectrophotometers 47. Cuvette 45 includes a hollow main body 121 with a lid 122 fixedly secured to the main body. A removable plug 123 extends through aperture 124 (FIG. 8) thereby closing and sealing the lid. A pair of reagent bags 125 and 126 are mounted in the cuvette main body 121 and are held in place by a pair of retaining walls 127 and 128. A bag of desiccant 129 is mounted to the bottom surface of lid 122 and absorbs any vapors within the cuvette thereby preventing the vapors from entering the bags of reagents 125 and 126.

Figure 9:
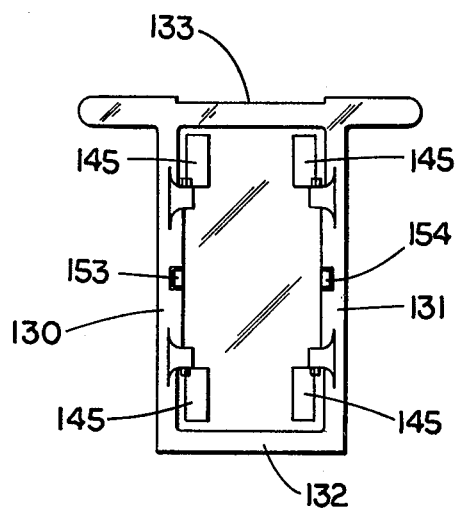
FIG. 9 is a top view of the main body of the cuvette taken along the line 9—9 of FIG. 8 and viewed in the direction of the arrows.

Main body 121 includes a pair of side walls 130 and 131 (FIG. 9) integrally joined to a pair of end walls 132 and 133. In one embodiment, the main body was produced from a clear plastic material, such as an Acrylic, providing excellent ultraviolet transmission capability. The material was chosen for its ability to pass the entire light specimen (wave lengths from 340 to 610 nanometers) with at least 80% transmittance. Thus, the specimen while within the cuvette may be measured by a spectrophotometer at all of the above mentioned five wave lengths.

Walls 130 and 131 extend parallel from the top edge 134 to the bottom 135 of the main body. Top edge 134 (FIG. 8) extends in a general rectangular configuration forming an opening 136 which is closed by lid 122. A bottom wall is integrally attached at the bottom of the cuvette main body to walls 130 to 133. End walls 132 and 133 (FIG. 8) extend parallel from the top edge 134 of the cuvette main body downwardly to location 137 and then converge inwardly a short distance and then extend downwardly in a parallel relationship until they reach the bottom 135.

Side walls 130 and 131 have mutually facing surfaces with four parallel grooves 138 through 141 (FIG. 8) extending from the top edge 134 downwardly to location 137. Retaining walls 127 and 128 are sized to fit within and be secured by grooves 138 through 141 thereby forming a pair of pockets positioned between end walls 132 and 133 and retaining walls 127 and 128. Reagent bags 125 and 126 fit within the pockets. A mixing chamber 142 (FIG. 7) is thereby formed between the retaining walls and extends downwardly from the lid to the bottom wall of the cuvette.

The reagent bags 125 and 126 are of identical design and thus, the following description as to the bag 125 applies equally to bag 126. Reagent bag 125 is made by scoring a flexible film material with a laser to form a linear depression along approximately the entire length of the film. The film is folded along the linear depression such that there are two sides of approximately equal dimensions and such that the bottom edge of the folded film is the laser scored linear depression. Portions of the two sides of the film are sealed together at predetermined intervals to form a bag having one opened end. The reagent is injected into the bag through the opening which is then sealed. The bags are then inserted into the cuvette and eventually into the centrifuge and violently rupture at a predetermined level of centrifugal force with the reagent then passing from the bag into the mixing chamber of the cuvette thereby mixing with the specimen provided therein. Such a bag is disclosed in the commonly assigned U.S. Patent application Ser. No. 563,562 entitled BAG.

Figure 8:
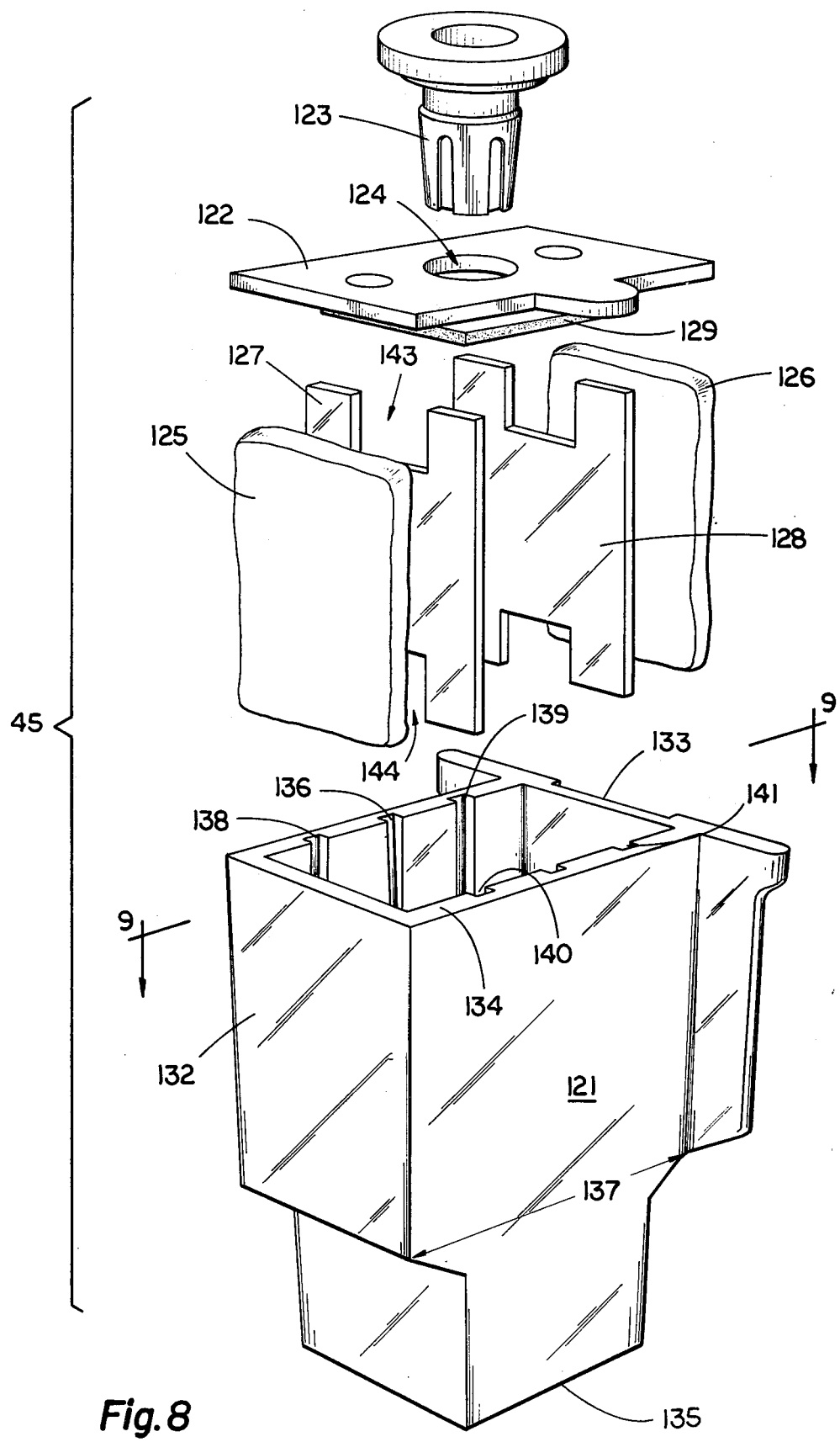
FIG. 8 is a perspective exploded view of the cuvette.

Each retaining plate is provided with a top and bottom recess defining openings 142A and 142B to allow the reagent within the adjacent reagent bag to flow into the mixing chamber. For example, retaining walls 127 and 128 are provided with recesses 143 and 144 (FIG. 8). Each end wall 132 and 133 is provided with a ledge 145 to seatingly receive a reagent bag. For example, end wall 132 (FIG. 7) is provided with a ledge 145 to seatingly receive the bottom edge of reagent bag 125 thereby positioning the bottom edge of the reagent bag slightly higher than the bottom edge of retaining wall 127. Walls 132 and 133 are provided with recesses which extend from beneath the reagent bags and beneath the retaining walls and into the mixing chamber. For example, end wall 132 is provided with recess 146 (FIG. 7) which directs the reagent into the mixing chamber. Of course, the bottom portions 147 of end walls 132 and 133 (FIG. 7) are completely transparent allowing analysis of the liquid specimen between the end walls by a spectrophotometer as shown by arrow 148.

Walls 127 and 128 are spaced apart respectively from walls 132 and 133 to provide oversized pockets receiving the reagent bags. The reagent bags are not supported by walls 127 and 128 and therefore expand under the force of the centrifuge. The liquid reagent in each bag acts as a column of liquid on the bottom edge of the bag causing the eventual bursting of the bag. Walls 127 and 128 are, however, located sufficiently close to walls 132 and 133 so as to prevent the bags from slipping into the mixing chamber.

The bag of desiccant 129 includes a plastic container fixedly secured to lid 122 by means such as by adhesives. The plastic container holds conventional desiccant to absorb the vapors within the cuvette. The reagent bags as well as the desiccant container are produced from a plastic film. Thus, the plastic used to produce the reagent container has a higher permeability as compared to the plastic body of the reagent bags thereby insuring that the vapors are absorbed by the desiccant container and not the reagent bags.

The bag of reagent may be produced from Aclar film which has a low permeability. The total amount of vapor evaporated through the film into the cuvette from the bag of reagent may be 40 microliters per year. This vapor could continue to shorten the shelf lyophilized enzyme material enclosed in the cuvette. In order to prevent the vapor from being absorbed by the lyophilized enzyme material, a vapor absorbing chemical is packaged in the desiccant container which is produced from plastic having a high permeability.

Figure 10:
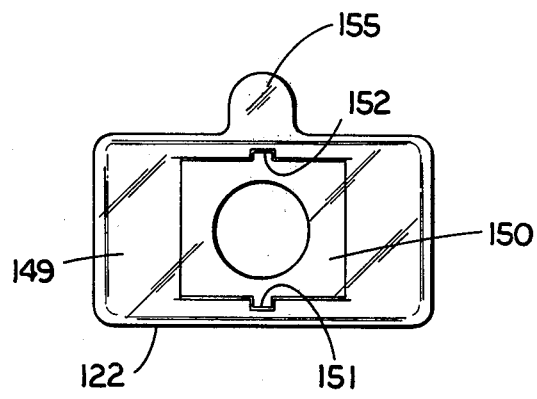
FIG. 10 is a bottom view of the cuvette lid shown in FIG. 8.

Lid 122 (FIG. 10) has a bottom surface 149 with a generally rectangular projection 150 provided thereon which extends into the cuvette main body. A pair of tabs 151 and 152 are provided and are complementarily received by a pair of notches 153 and 154 of side walls 130 and 131 (FIG. 9) to prevent relative motion between the lid and the cuvette main body. The lid may be sealed to the cuvette main body by means such as ultrasonic welding.

Figure 11:
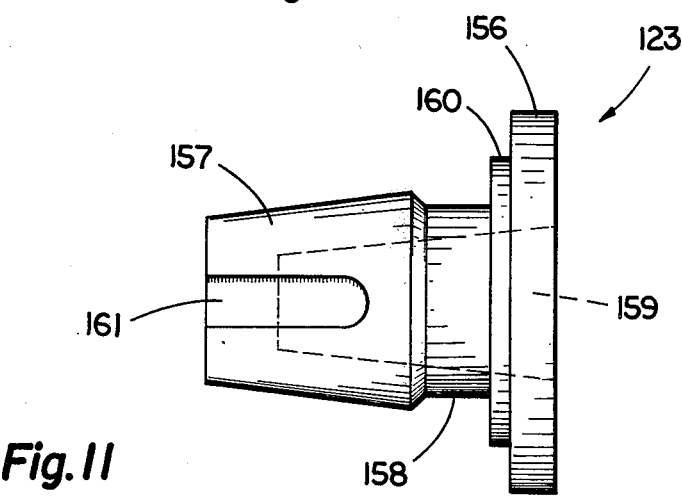
FIG. 11 is an enlarged side view of the plug shown in FIG. 8.

Plug 123 is produced from a semi-flexible material, such as rubber. Integrally attached to the top wall 156 of the plug is a tapered and cylinderical bottom portion 157 being attached to the top wall by a necked down portion 158 (FIG. 11). An indentation 159 extends through the top wall and into the tapered portion of the plug allowing the tapered portion to compress as the plug is forced into the aperture of the lid. Of course, indentation 159 does not extend completely through the plug and thus, the plug seals the cuvette when inserted through the lid. The largest diameter of the tapered portion 157 is greater than the diameter of the lid aperture and will therefore compress as the plug is inserted into the lid. When plug 123 is completely inserted into the lid aperture, the lid is positioned adjacent to the necked down portion 158. A cylinder washer 160 is integrally formed on the bottom surface of top wall 156 of the plug to thereby space top wall 156 slightly above the top surface of lid 122. It is therefore possible to insert a tool beneath the top wall of the plug and to subsequently pry the plug from the lid. Tapered portion 157 is beveled immediately adjacent necked down portion 158 to prevent the plug from accidental disengagement from the cuvette. A plurality of grooves 161 are provided in the outer surface of the tapered end of the plug to facilitate the compression of the tapered end as the plug is inserted into the cuvette. In certain cases, a bag of reagent will not be inserted into the cuvette and instead, the reagent will be placed into the cuvette being free to move throughout the main body of the cuvette. In the event the reagent is to be freeze-dried, then plug 123 is partially inserted into the cuvette allowing moisture to be withdrawn through the lid via grooves 161 until eventually the plug is fully inserted. Thus, grooves 161 allow moisture to escape the cuvette during the lyophilization process.

Figure 12:
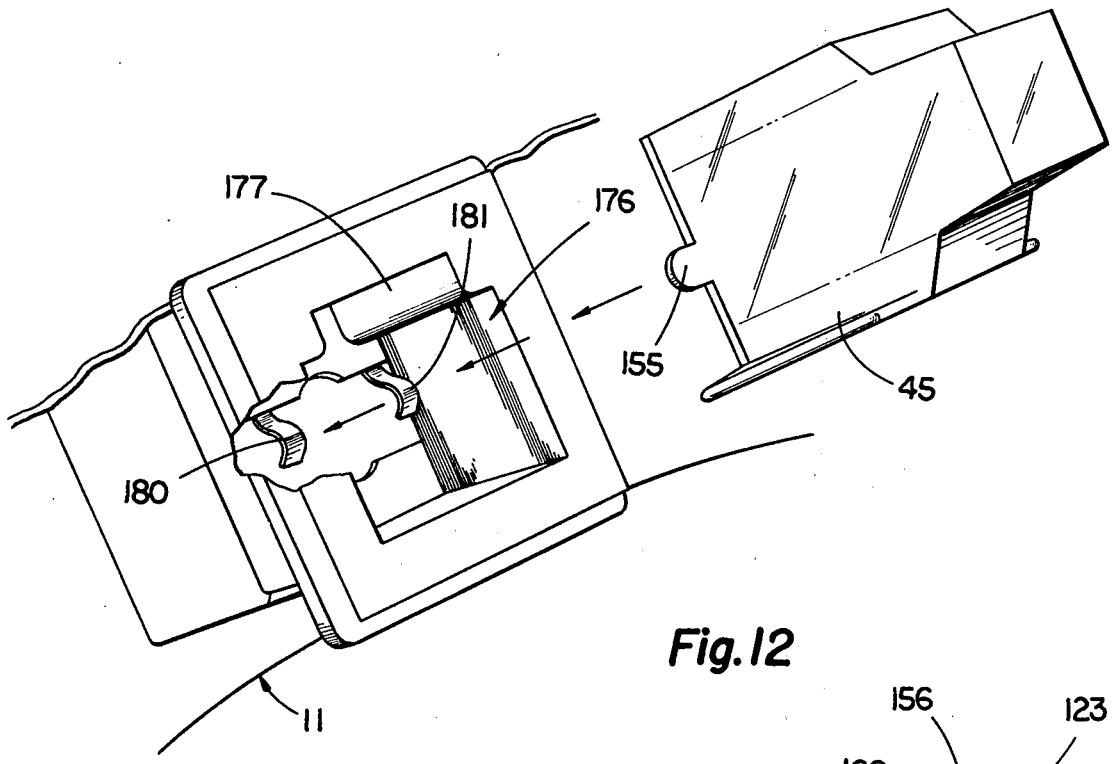
FIG. 12 is a fragmentary perspective view of the cuvette of FIG. 7 being inserted into a microdilution apparatus of the present invention.

A pair of flanges 170 and 171 are integrally attached to end wall 133 (FIG. 7). Flanges 170 and 171 project outwardly of side walls 130 and 131 and are provided to receive various markings in areas 172 with the markings indicating the test name, a test number and binary codes. Additional information may be marked on areas 187 and 188 on lid 122 (FIG. 7). The flanges extend outwardly of the main body of the cuvette to allow optical reading of the test codes and to permit insertion of the cuvette into a test receptacle in only one given direction. Shown in FIG. 12 is a portion of microdiluter apparatus 11 including a receptacle 176 for receiving cuvette 45. End 177 of receptacle 176 is of a smaller dimension and thus can receive the cuvette only if end wall 132 is inserted into the receptacle adjacent end 177 as contrasted to end wall 133 which is larger including flanges 170 and 171. Thus, the cuvette may be inserted into the test receptacle only when the cuvette is oriented in a given direction with respect to the receptacle.

Various tests are conducted on the specimen within the cuvette. Certain tests require the specimen to be diluted by a greater amount as compared to other tests. Likewise, varying amounts of specimen are used depending upon the particular test. The cuvettes are premarked in areas 172 both in digital code and in printing to indicate the proper cuvette to be used with the particular test. Once plug 123 is removed, the diluted specimen may be inserted into the cuvette and the plug reinserted through the lid. To insure that the correct dilution of the specimen is provided as required by the particular test, a tab 155 extends outwardly from lid 122 and outwardly of the cuvette main body. Except for tab 155, the lid is symmetrical and thus, the lid may be originally installed either positioning tab 155 adjacent side wall 130 or adjacent side wall 131. In those tests requiring the specimen to be diluted only a small amount, tab 155 is positioned adjacent, for example, side wall 130 whereas tab 155 is positioned, for example, adjacent side wall 131 when the particular test requires a large dilution of the specimen. Apparatus 11 automatically provides the correct amount of specimen dilution depending upon the orientation of tab 155.

A pair of microswitches 180 and 181 are positoned at the bottom of test receptacle 176 and are contacted and activated by tab 155 depending upon the orientation of tab 155. For example, by inserting the cuvette into the test receptacle as shown in FIG. 12, tab 55 will contact switch 180 thereby activating the diluter operated by switch 180. The cuvette is then withdrawn and the appropriate amount of diluted specimen is then inserted through the lid by the diluter. Likewise, tab 155 may be positioned on the opposite side of the cuvette as compared to FIG. 12 with the result that switch 181 will be activated by the tab providing for the correct amount of dilution once the cuvette is withdrawn from the test receptacle and connected to the diluter.

The microdilution apparatus 11 comprises two pump sections 190 and 191, each of which has an aspirator-dispensor hose and tip 192 and 195 and each of which has a power indicator light 196 and 197 and a start button 200 and 201. Mounted between the pump sections 190 and 191 is a plug remover 202 which consists of a web member 205 having a slot 206 therein for receiving the necked down portion 158 of the plug 123. Each of the pump sections 190 is a commercially available device, the function of which is to aspirate a predetermined volume of fluid in a container and to dilute the predetermined volume of fluid by a predetermined specific ratio and to then dispense the diluted fluid volume.

In order to operate the microdilution apparatus 11 the proper cuvette for the test to be performed is inserted into the receptacle 176 as shown in FIGS. 12 and 14. Depending on the location of the tab 155 on one side or the other of the cuvette the pump section 190 or 191 will be actuated. Thus switch 180 connects the power to pump section 190 and switch 181 connects the power to pump section 191. Assuming the tab 155 is located as in FIG. 12, the pump section 190 will be turned on and the power indicator light will energize which notifies the operatore that he must use the pump section 190 with its aspirator-dispensor-hose and tip 192. Of course, if he attempts to use the hose and tip 195, it will not operate because the power to the pump section 191 has not been turned on.

The operator inserts the hose tip 192 into the serum receptacle and presses the start button 200 causing the pump section 190 to automatically aspirate the correct amount of serum. The operator removes the hose tip 192 from the serum receptacle and wipes the tip with a lint-free tissue. The cuvette is removed from the receptacle 176, and the plug removed by insertion of the neck 158 of the plug into the slot 206 and a downward movement of the cuvette. The cuvette is then placed under the tube 192 and the start button 200 pressed again. The cuvette is held under the tube until the liquid flow stops whereupon, after tip wiping, the plug is replaced in the cuvette and the cuvette is ready for insertion into the test apparatus 10.

Preferably the blood analyzer system is operated on an automatic basis. In one embodiment of the invention, there are seven cycles to the complete centrifuge spectrophotometer incubator operation. These cycles are (1) mix-preincubation; (2) low-speed-1000 rpm preincubation; (3) read blank and store in memory; (4) high-speed bag break; (5) reagent mixing; (6) reaction cycle; and (7) read final results. The instrument can be set up to automatically require different total elapsed times to carry out the above listed steps. However, in one embodiment of the invention, the total elapsed time from the insertion of the cuvette until the reading of the final result is 15½ minutes. In the mix preincubation cycle, the apparatus mixes the diluted serum in each cuvette with any reagents that may be present in the cuvette and outside of the reagent bags. Also, the sample is incubated or brought to correct temperature in this cycle. Mixing is carried out by repeatedly reversing the direction that the motor 20 rotates the rotor 25. The mix cycle goes on for 2½ minutes from start. In the next cycles the low-speed (1000 rpm) preincubation cycle, the motor rotates the rotor in one direction and the sample continues to be incubated. Also in this cycle which lasts for three minutes, the instrument reads the code of the cuvette in the one of the areas 172 and stores the code of the cuvette, telling the instrument which test is being performed and whether the test is an endpoint of a kinetic test.

The coded cuvette also tells the spectrophotometer portion of the instrument what wave length should be selected for reading the test. In said specific embodiment of the invention the instrument reads the absorbance of each sample and stores the result in its memory 2½ minutes after the "low-speed cycle" has begun. This figure is the serum blank figure.

At the completion of the "low-speed cycle" 5½ minutes after the start, the instrument accelerates into the high-speed bag break cycle. The acceleration of the rotor to 10,000 rpm causes a weakened section of the bags of the reagents to fail and the reagent flows through the openings 142B into the optical portion of the cuvette, mixing with the serum therein. The time alloted in said specific embodiment of the invention for this bag break cycle is one minute. The instrument then (at 6½ minutes after start) goes back into a second mix cycle wherein the rotor is reversed repeatedly by the motor. This mix cycle lasts for one minute whereupon the motor again goes into a low speed 1000 rpm forward cycle, which is maintained until all cycles are completed.

The instrument function during the reaction cycle depends on the mode of operation. If the instrument is being operated in the percent transmission or absorbance mode, the instrument reads and prints the percent plus or minus or absorbance of all eight rotor positions at one-minute intervals from 8½ to 15½ minutes after start. On the other hand, if the instrument is being operated in the concentration mode, the function depends on the tests that are being performed. If all end point tests are being performed, the instrument takes no readings until 15½ minutes after start at which time it reads and stores the absorbance for each sample. The rotor position, test number and concentration which the instrument calculates from the stored standardization absorbances and the final absorbances is printed.

If, on the other hand, kinetic tests are being performed, the instrument reads all eight rotor positions at one-minute intervals. The absorbances at minute 8½ are read and stored. The absorbances at minute 9½ are read and stored. The absorbances are then subtracted. If the absorbances vary by less than ±10%, the instrument takes the second absorbance and multiplies it by the extinction coefficient stored in its memory. The concentration is then immediately printed. If the difference between the two absorbances is more than ±10%, then the instrument reads the absorbance at 10½ minutes and compares the 9½ minutes and the 10½ minutes absorbances. If the absorbances differ by less than ±10% a concentration is printed. However, if the absorbances do not differ by ±10%, then the instrument goes on to read a further absorbance at minute 11½. If the instrument does not observe a less than ±10% difference in absorbances by the end of the eight-minute reaction cycle, that is, by the time the instrument reaches minute 15½, the instrument will calculate the concentration from the last absorbance and print in red ink.

Kinetic and endpoint tests may be mixed in any numbers. In other words, all of the stations may have kinetic tests run at them, that is, eight kinetic tests with eight cuvettes or all of the stations may have endpoint tests run at them or any number of each may be run, such as seven and one; five and three; and so on. The instrument may also be operated in the stat mode. In the stat mode the instrument offers the user the opportunity to perform a test or tests that have not been previously calibrated. This mode provides a means for simultaneous calibration standardization and reading of unknowns. In this mode the cuvettes in positions 1 and 2 in the rotor are offered to the instrument as 0.0 concentration. The cuvettes in rotor position 3 and 4 are offered to the instrument as standard concentration samples. The cuvettes in rotor positions 5–8 are offered to the instrument as unknown samples. At the end of the reaction cycle the rotor number, the test number and the concentration are printed for each of the unknowns.

Figure 16:
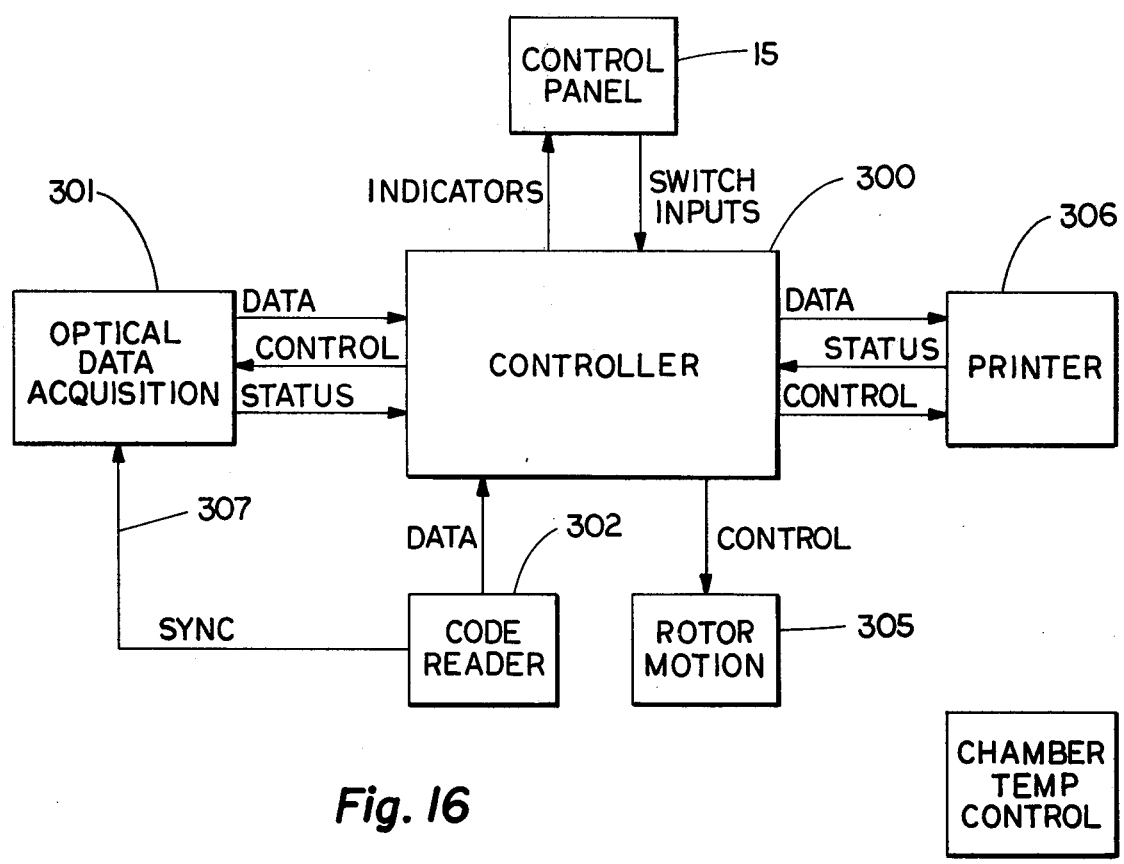
FIG. 16 is a schematic drawing of the control system for the centrifuge spectrophotometer incubator apparatus 10.
Figure 17:
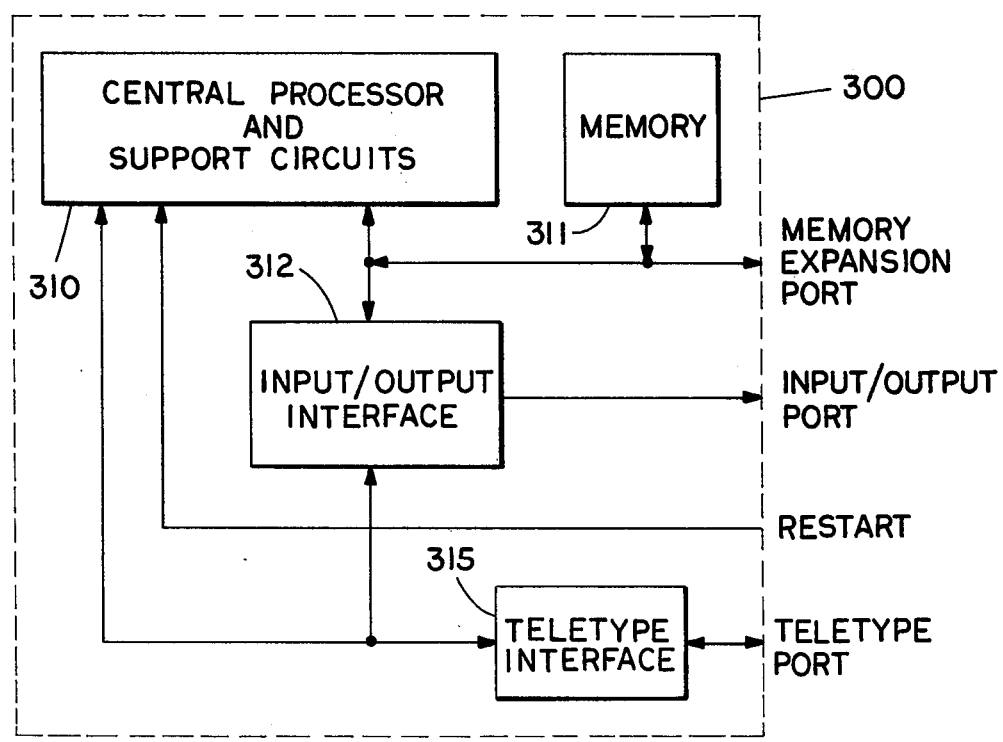
FIG. 17 is a schematic drawing of the controller portion of control system of FIG. 16.

In the preferred embodiment of the invention, all operations of the system are a function of the controller 300 (FIG. 16) with the exception of rotor temperature control. Data is input from the control panel 15, optical data acquisition section 301, and cuvette code reader sections 302 for interpretation and processing. Control signals are sent by the controller to the control panel, optical data acquisition section, rotor motion section 305 and printer section 306. Data results of the various test modes are output to the printer section. Operations information is input and instrument status is output via the control panel 15. Signals from the panel switches to the controller select the type of operation to be executed and input the data constants required for calculating concentration for specific tests. Status signals from the controller operate lights on the control panel 15 indicating when the instrument is incubating the samples, breaking the reagent bags, mixing solutions or reading optical data.

The controller selects the desired test source by sending a code to the optical data acquisition block 301. Test source selection must be synchronized with the angular position of the rotor by the controller and a synch pulse 307 from the rotor position module so that the correct optical channel is read when the appropriate cuvette is in its optical path. The selected optical data is either linearly or logarithmically processed by the acquisition block 301 yielding an electronic signal proportional to optical transmittance or absorbance of the test solution. This signal is further converted to a twelve bit digital representation. A status signal to the controller indicates when this conversion is finished allowing the transfer of the twelve bit data to the controller.

Cuvette codes are sensed by an optoelectronic circuit within the code reader section 302 and transferred upon request, as digital information, with the associated rotor position number to the controller. Rotor motion is controlled by signals from the controller to the rotor motion section 305. Digital commands are translated to motion of the universal motor 20 and command it to rotate forward at 1000 rpm, reverse at 1000 rpm and forward at 10,000 rpm. Mixing of the serum/reagent solution is accomplished by alternate forward and reverse commands; optical data acquisition is done while maintaining a constant forward 1000 rpm; and reagent bag break is accomplished at a forward 10,000 rpm.

All communications of output data, in the form of calibration references, sample optical data, or calculated chemical concentrations to the operator, are made via an alphanumeric printer. A heading designating the type of data is printed followed by the appropriate data. When calculating concentration the rotor position, the test type nmemonic of the cuvette at that position, and the results are printed. The only function not controlled centrally is the rotor chamber temperature. This is the function of chamber temperature control. Using the thermistor sensors and the heater strip 46, temperature is regulated in the chamber at 37° C. ±0.3° C.

The controller 300 is a complete computer on a single printed circuit board. On the board is a central processing unit (CPU) 310, with arithmatic capability, a memory 311, clock mechanism and input-output circuits 312 including a complete serial interface for a teletype. Connectors provide expansion capability as well as means for integrating the controller into a multi-board system. In one specific embodiment of the invention the CPU is a microprocessor Model No. 8008 of Intel Corporation, Santa Clara, Calif. Memory consists of two types of storage elements: non-volatile program and volatile data storage. The program instruction codes which are interpreted by the microprocessor for process control are stored in the MOS Read Only memory. Data such as required constants, acquired data, or calculated data is stored in MOS Random Access memory. The input/output interface consists of an eight line bidirectional data multiplexer and an input/output instruction decoder. The multiplexer sends and receives data from the microprocessor to all the peripheral circuits. Decoding of an input/output instruction enables the multiplexer and the peripherals to select the proper data sent to or received from the microprocessor.

The optical data acquisition section is shown in greater detail in FIG. 18. The light source 51 for each wave length is a tungsten-halogen lamp. The various wave lengths 340, 405, 540, 580 and 610 manometers are achieved by interference filters 55. The focusing of the lights 51 on the sensors 50 in each case generates a current proportional to the incident light which is converted to a voltage signal by an operational amplifier circuit. A digital signal 317 from the controller 300 to an analogue switch 320 selects one of the five signals for further processing. The selected signal is further amplified by the operational amplifier circuit 321. Because the signals coming from the optical sensors are pulses corresponding to cuvettes moving through the optical paths, a sample-and-hold circuit 322 is necessary to stabilize the signal during analogue-to-digital conversion. A synch signal 325 from the light and phototransistor assembly 62 triggers the sample-and-hold circuit when the cuvettes are aligned with the optical paths.

The sampled signal is then sent to both a linear amplifier 327 and a logarithmic amplifier 300. The linear amplifier effects a scale factor multiplication necessary if sample transmittance data is required. The logarithmic amplifier produces a two decade logarithmic function of the sampled signal for absorbance data acquisition. A digital signal 331 from the controller to an analog switch 332 selects either the linear or logarithmic signal for conversion by the analog-to-digital converter 335 (ADC). A completed conversion is indicated to the controller by a digital signal 336 and a 12 bit binary representation is then available to the controller. Because the controller with the Intel 8008 micro-computer is an eight bit parallel, byte serial system, the twelve bits are transmitted in two groups, the upper eight and the lower four from the ADC. The selection of the two bytes is controlled by a digital command 337 from the controller.

Rotor position is sensed by optoelectronically detecting the holes 60 and 61 in the rotor rim corresponding to the eight cuvette positions. A reference position is indicated by the normal hole 60 being followed closely by the secondary hole 61. The light and phototransistor assembly 62 produces a pulse as a result of the passage therebetween of each hole 60 triggering a fixed period one shot circuit 340 (FIG. 19). The period is the speed of the rotor rim divided by the distance along the rim between the normal and secondary holes 60 and 61. If a second pulse occurs within the period of the one shot, a signal is generated to reset the position counter 341. In this manner the count is reset and synchronized during each rotor rotation.

The cuvette synch pulse or rotor position synch 325 is used to strobe information from the eight optoelectronic sensors 41 for the cuvette code into a register 342. The code contained, at any given time, in the code register corresponds to the cuvette held in the rotor position indicated in the counter. The cuvette (rotor position) synch pulse 325 is also sent to the optical data acquisition section as shown in FIG. 18 to trigger the sampling of the optical signals.

Figure 20:
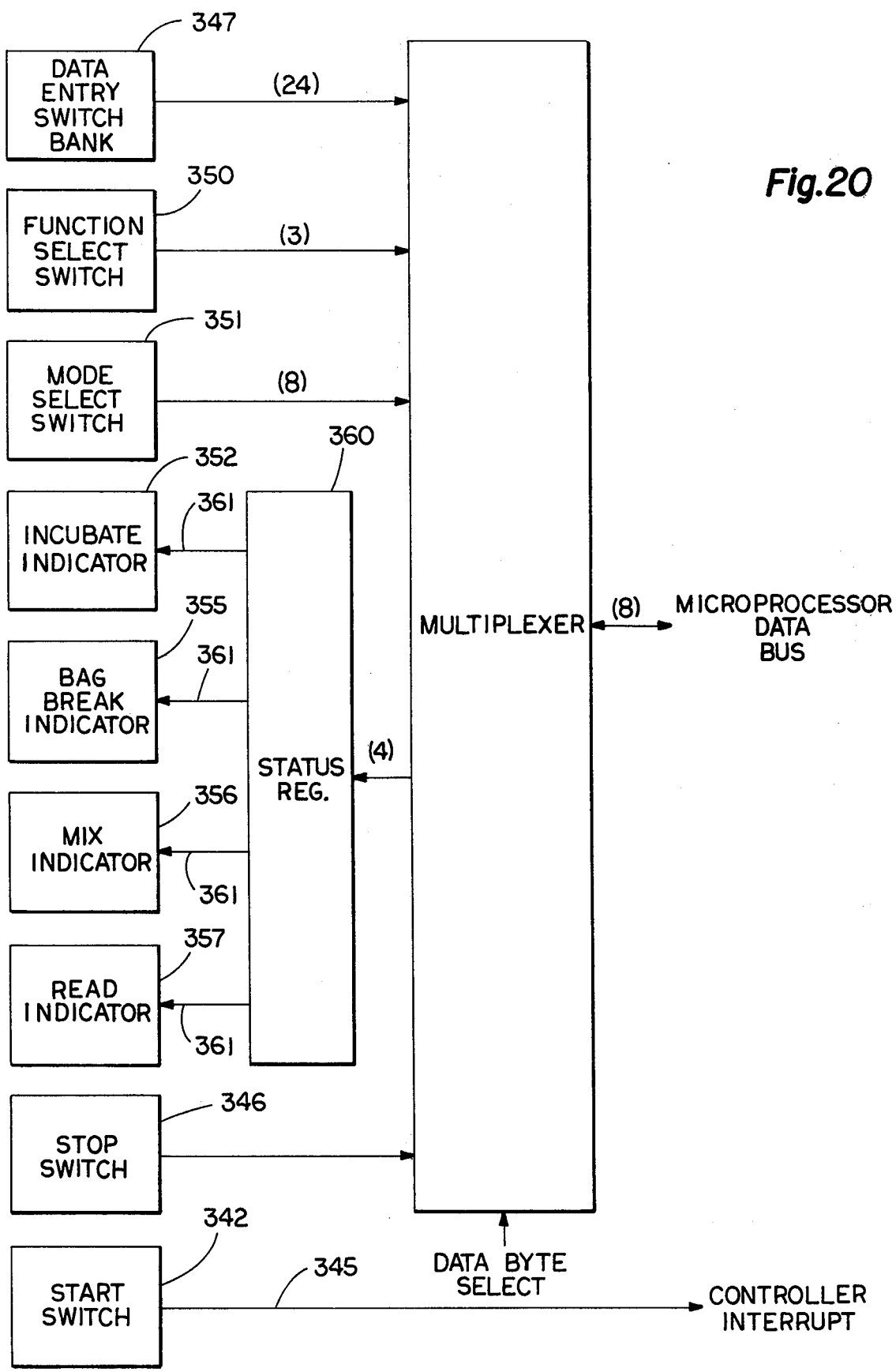
FIG. 20 is a schematic drawing of the control panel of the apparatus.
Figure 21:
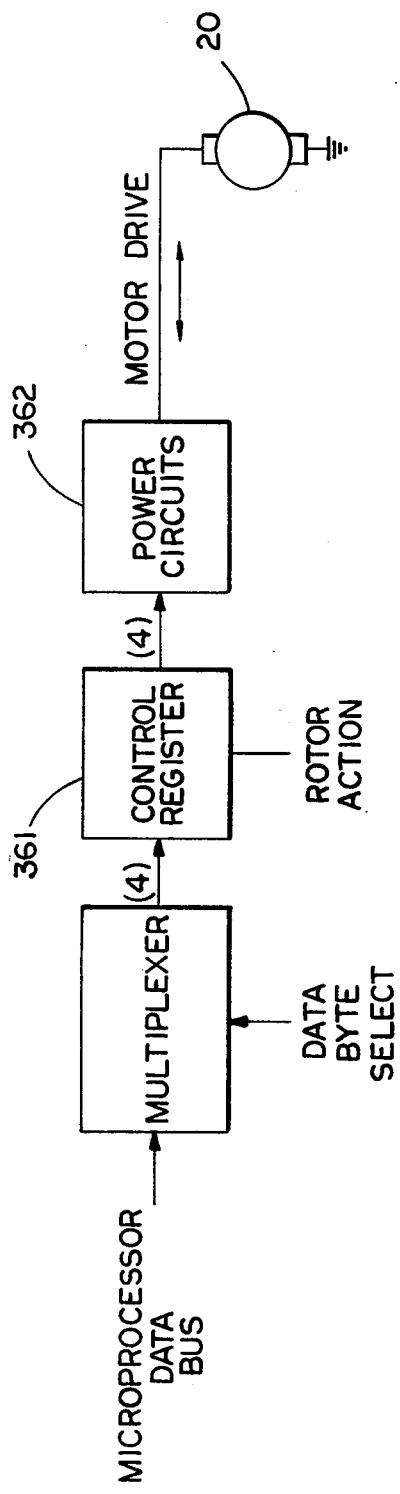
FIG. 21 is a schematic drawing of the rotor motion circuit of FIG. 16.
Figure 23:
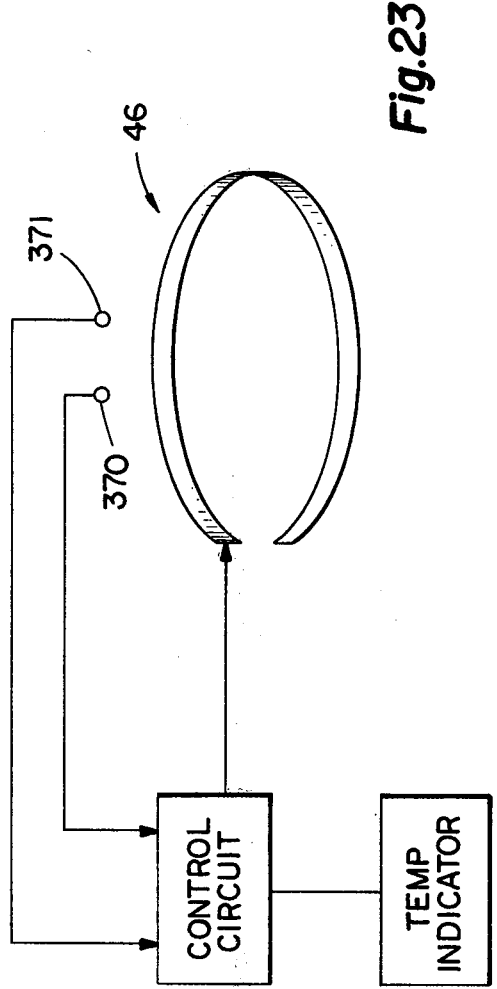
FIG. 23 is a schematic drawing of the temperature control circuit of the apparatus.
Figure 22:
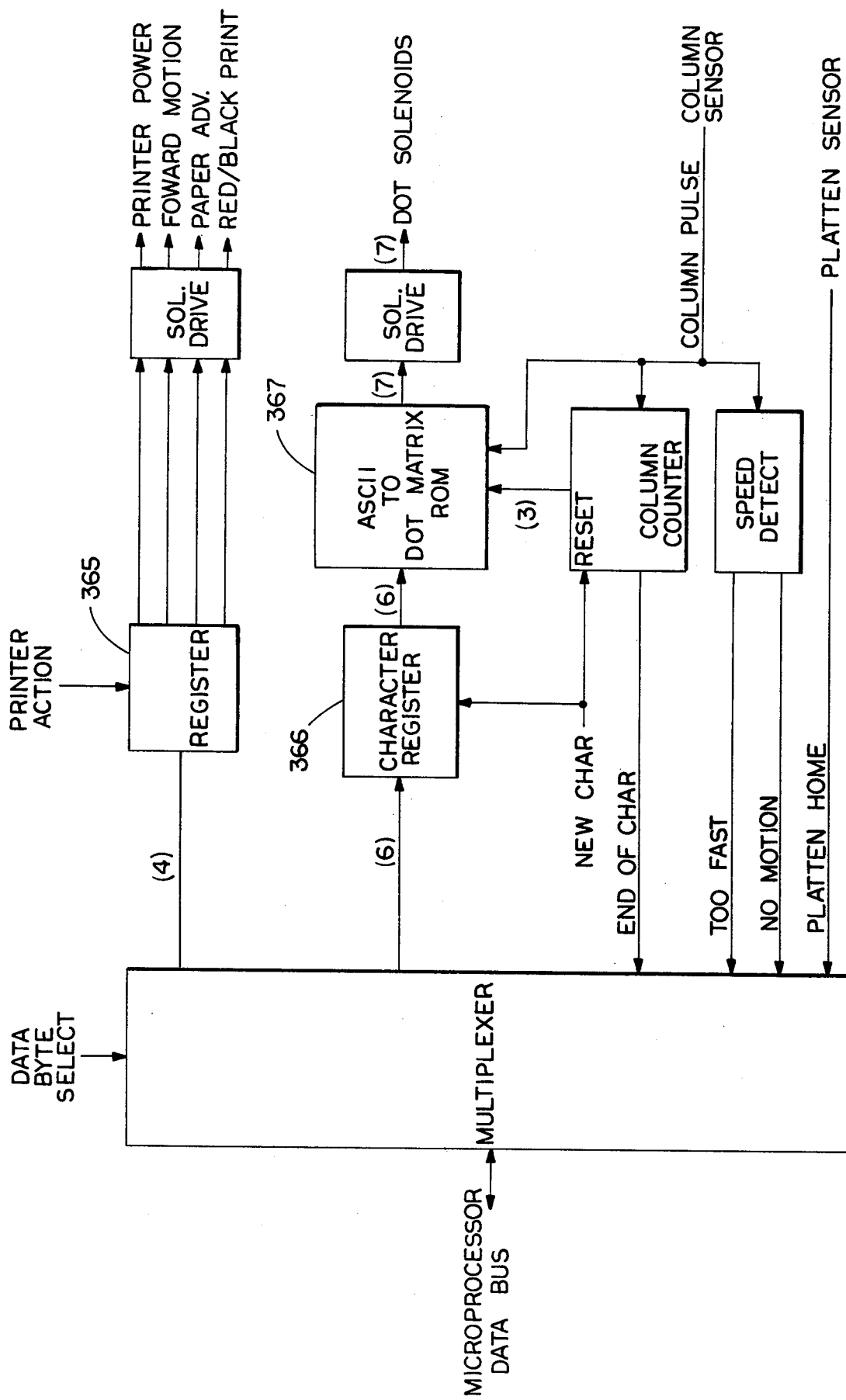
FIG. 22 is a schematic drawing of the printer circuit of FIG. 16.

Data entry, function and mode selection, instrument status display and starting and stopping machine action is carried out by the control panel 15 shown schematically in FIG. 20. Initiation of a machine cycle is effected by activating the start switch 342 which asserts the controller interrupt input causing program restart. Depression of the stop switch 346 is sensed over the data bus to halt any operation. Data entry, such as test numbers, kinetic coefficients, and endpoint standards, is made by a bank of six thumbwheel switches 347. These are multiplexed, upon demand, over the data bus to the controller. The type of test or calibrate operation desired is selected by the function select switch 350 and mode select switch 351. Their outputs are multiplexed, upon demand, over the data bus to the controller. System operation during a test cycle is shown by the status indicators, incubation 352, bag break 355, mix 356 and read 357 which are operated by selectively setting the status register 360 via the data bus. The register outputs 361 drive indicator lamps.

Rotor motion is achieved by controller caused action on the motor 20 which is a series wound universal motor. The motor may be, for example, a 1/7 HP 1.9 Amp Bodine Universal Motor No. NSE 13 manufactured by Bodine Electric Company of Chicago, Ill. 60618. Motion required for mixing reagent and sample is obtained by alternatively driving the motor in forward and reverse direction. The radial acceleration required to rupture the reagent bags is supplied by a very high rotational velocity of 10,000 rpm. A constant stable forward rotation of 1000 rpm by the motor is required during the time the cuvette absorbances are sampled. The controller asserts four command lines, Enable, Forward, Reverse and Hi Speed, by loading the control register 361 via the data bus. Enable is a qualifier for the remaining three commands and must be asserted for any action to take place. These commands generate a signal to the motor, Motor Drive, through the power circuits 362. The polarity and magnitude of this signal determines the direction and speed of the motor and, hence, the rotor.

Display of observed and calculated data is accomplished by a controller operated dot matrix printer. The mechanical portions of the printer are well known and commercially available in the form of, for example, a Victor Dot matrix printer model IPM 130, 115 volts 60 HZ Cycles manufactured by Victor Comptometer Corporation of Chicago, Ill. 60613. Six bit ASCII characters are sent serially to the printer electronics which operates the printer by selectively driving a column of seven solenoid hammers against ribbon and paper as the column passes horizontally over the paper. In this manner characters are formed on a 5 × 7 matrix of ink dots. All action of the print mechanism is a function of the controller. Four action-causing signals, printer power, forward motion, paper advance, and red/black print, may be asserted by loading of the motion control register 365 via the data bus by the controller. Printer power activates a triac to deliver power to the printer electromechanics. Forward motion activates a clutch enabling a motor to drive the print head in a right-to-left motion. Assertion of paper advance slews paper upward. Red/black print selects red print when asserted by activating a solenoid to position the two color print ribbon.

The character to be printed is loaded into the character register 366, the outputs of which drive the upper address inputs of a ROM 367. Each character is assigned a set of five memory locations. These are selected by the coincidental input of the character's ASCII code and a count pointing to the desired column within the 5 × 7 matrix. The count required to designate print columns is generated by 170 spatially equal pulse which occur as the print head passes over the print surface. Also generated by these pulses is a constant width pulse which, if coincident with valid character data and column count, causes the appropriate Dot Driver outputs to be asserted. These outputs drive hammer solenoids to cause printing.

Several flags are required by the controller for proper operation. When the column counter has cycled through the count of five columns it signals its readiness for the next character by asserting the End of Character flag. No Motion signals that the print head is not moving. This is generated by print column pulses and indicates that the print head has stopped motion after printing a line and is ready for the first character of the next line. Also generated by the print column pulses is a flag indicating that the print head, on its spring driven return to the rest position, is traveling too fast. The controller's response would be to pulse the forward motion command to slow this reverse motion. When slewing paper Platten Home signifies that the paper has moved the distance required for a new line.

To insure stability of the chemical reactions to be observed, temperature within the rotor chamber is maintained at 37° C. ± 0.3° C. This is accomplished by an electronic system utilizing two thermistors as the sensing elements and a silicone encased nichrome heating element as the energy source. The system monitors the temperature at start up with thermistor 370. The placement of the sensor enables the temperature to rise from ambient to $\approx 30°$ C. Use of the second thermistor 371 is for finer control at the desired 37° C.

Heat is generated by sourcing current through the nichrome wire elements 46. These are placed around the chamber periphery (FIG. 2) causing heat to radiate inward throughout the chamber. An indicator lamp on control panel 15 shows when the temperature is within the desired limits of 37° C. ±0.3° C. The control of this indicator is a function of the Control Circuit through use of the thermistors. The Control Circuit is a switching configuration. Current to the elements is turned completely on or off as a function of the two sensors. It also controls the Temperature Indicator as a function of the sensors.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. Apparatus for performing chemical tests comprising:
   (a) a centrifuge having a rotor, said rotor including cuvette-retaining means;
   (b) a cuvette having a test chamber portion therein and test information coding thereon, said cuvette being mountable into said cuvette-retaining means;
   (c) a spectrophotometer mounted on said centrifuge and adapted to read the test chamber portion of said cuvette;
   (d) means for reading the test information coding on said cuvette, said code reading means being mounted on said centrifuge;
   (e) and means for receiving the signal from said code reading means and from said spectrophotometer and for displaying the test result appropriate for said test information coding.

2. The apparatus of claim 1 additionally comprising: a microdiluter including two pump sections of different dilution capability, each having an aspirator dispenser hose;
   said microdiluter having a receptacle therein which is shaped to permit insertion of said cuvette only when the cuvette is in a given orientation relative to said receptacle;
   a pair of switches mounted on said microdiluter, one associated with one of said pump sections and the other associated with the other of said pump sections; each of said switches being positioned to be actuated by tab on the cuvette with the tab being oriented in accordance with the desired dilution of the liquid substance to be inserted into the cuvette.

3. The apparatus of claim 2 wherein:
   said cuvette is shaped for insertion into said receptacle only when the cuvette is in a given orientation relative to said receptacle;
   a tab mounted on said cuvette and oriented to actuate one or the other of said switches in accordance with the desired dilution of the liquid substance to be inserted into the cuvette.

4. The apparatus of claim 3 wherein said cuvette comprises:
   a hollow main body adapted to receive a liquid substance, said main body including at least two opposed end walls to allow testing of said liquid substance by a spectrophotometer while said liquid substance is within said main body;
   a first bag of reagent positioned within said main body, said bag having bursting means operable to allow said reagent to escape said bag and mix with said liquid substance upon exposing said main body to a predetermined amount of centrifugal force;
   a lid sealingly mounted on said hollow main body.

5. The apparatus of claim 4 and further comprising:
   desiccant means mounted in said hollow main body being operable to absorb vapor within said hollow main body prior to said vapor being absorbed by said bag of reagent.

6. The apparatus of claim 5 wherein:
   said bag of reagent includes an outer main body of plastic sheet of a predetermined permeability;
   said desiccant means includes a container of desiccant attached to said lid, said container includes an outer wall of plastic of a permeability higher than said predetermined permeability of said bag of reagent.

7. The apparatus of claim 4 wherein:
   said main body includes a flange extending outwardly therefrom allowing the insertion of said cuvette into said receptacle only when said main body is in a given orientation relative to said receptacle, said flange being adapted to engage said rotor for locking said cuvette in said rotor, said test information coding being on said flange.

8. The apparatus of claim 4 wherein:
   said lid has said tab mounted thereon extending outwardly of said main body, said lid being mounted to said main body to position said tab in a different orientation relative to said main body depending on the dilution and quantity of said liquid substance to be inserted into said main body.

9. The apparatus of claim 8 wherein:
   said lid includes an aperture extending therethrough; and further comprising:
   a removable plug mounted on said lid and sealing said aperture.

10. The apparatus of claim 9 wherein said cuvette has a further flange extending oppositely of said first mentioned flange, said rotor having hooking members thereon adapted to engage said flanges to hold said cuvette on said rotor.

11. Apparatus for performing chemical tests comprising:
    (a) a centrifuge having a rotor with a plurality of cuvette mounting stations thereon;
    (b) at least one reagent containing prepackaged cuvette having a test chamber portion therein and test information coding thereon and mounted on the rotor of said centrifuge at one of said stations; said test information coding corresponding to the test to be run in said cuvette;
    (c) a spectrophotometer mounted on said centrifuge and adapted to read the test chamber portion of said cuvette;
    (d) means for reading the test information coding on said cuvette, said code reading means being mounted on said centrifuge;
    (e) and means for receiving a signal from said code reading means and a signal from said spectrophotometer and for displaying the test result appropriate for said test information coding.

12. The apparatus of claim 11 wherein said rotor has a plurality of holes therein around the rotor with each hole located at a respective one of the various stations, a further hole located just adjacent to one of said plurality of holes, means for detecting and counting said holes as the rotor rotates for counting the positions, means for resetting the counting means actuated by the further hole, said counting means producing a synch pulse which is coupled to said code reading means for the strobing of information therefrom whereby the test result displayed is associated with the cuvette rotor position as well as the test information coding on the cuvette.

13. The apparatus of claim 11 wherein said means for receiving a signal from said code reading means and a signal from said spectrophotometer comprises a microprocessor, bags received within said cuvette and containing the reagents of said cuvettes, said bags being adapted to burst in response to a high rotary speed of said centrifuge rotor, said microprocessor having a memory which is programmed to move said rotor through a cycle which includes, in order, a back and forth mixing motion of the rotor, a low speed rotary motion of the rotor for reading the specimen in the test chamber portion without reagents, a high speed rotary motion for bag breaking and causing the reagents within the bags to flow into the test chamber portion, and a low speed rotary motion of the rotor for reading test results.

14. The apparatus of claim 13 wherein said memory has a random access portion wherein is stored required constants, acquired data and calculated data.

15. The apparatus of claim 11 wherein said means for receiving a signal from said code reading means and a signal from said spectrophotometer comprises a microprocessor, said apparatus including further spectrophotometers mounted on said centrifuge at various locations and adapted to read the test chamber of said cuvette, each of said spectrophotometers including filters of differing wave lengths for measuring the cuvette light passage at differing wave lengths, said microprocessor being arranged to reject all but one of the signals from the respective spectrophotometers as determined by the test information coding on said cuvette.

16. The apparatus of claim 11 wherein said means for receiving a signal from said code reading means and a signal from said spectrophotometer and for displaying comprises a microprocessor controlled dot matrix printer.

17. The apparatus of claim 11 wherein said means for receiving a signal from said code reading means and a signal from said spectrophotometer comprises a microprocessor, a control panel including means for the operator to enter data, select function and mode, and start and stop the apparatus, said control panel also including instrument status display.

18. The apparatus of claim 11 additionally including a heater in said centrifuge for controlling the temperature of the cuvette mounted on said rotor, thermistor means mounted in said centrifuge adjacent said rotor and coupled to said heater for maintaining the temperature of said cuvette at approximately 37° C.

19. Apparatus for performing chemical tests comprising:
    (a) a centrifuge having a rotor with a plurality of cuvette mounting stations thereon;
    (b) a plurality of reagent containing prepackaged cuvettes each having a test chamber portion therein and test information coding thereon and mounted on the rotor of said centrifuge each at a different one of said stations; said test information coding on each of said cuvettes corresponding to the test to be run for said cuvette;
    (c) a spectrophotometer mounted on said centrifuge and positioned to read the test chamber portion of each of said cuvettes;
    (d) means for reading the test information coding on each cuvette as it passes a given location on the centrifuge and for simultaneously reading the station at which the cuvette is mounted, said code reading means being mounted on said centrifuge;
    (e) and means for receiving a signal from said code reading means and a signal from said spectrophotometer and for displaying the test result for each station appropriate for said test information coding.

20. The apparatus of claim 19 wherein said spectrophotometer is one of a plurality of spectrophotometers, all of which are mounted on said centrifuge and adpated to read the test chamber portions of said cuvettes, said apparatus also comprising means for selecting the correct spectrophotometer readings for each station as indicated by the test information coding on the cuvette at each station for use in displaying the test result for each station.

21. The apparatus of claim 19 additionally comprising bags received within said cuvettes and containing the reagents of said cuvettes, said bags being adapted to burst in response to a high rotary speed of said centrifuge rotor, and means for causing said centrifuge to move through a cycle which includes, in order, a back and forth mixing motion of the rotor, a low speed rotary motion of the rotor for reading the specimen in the test chamber portion without reagents, a high speed rotary motion for bag breaking and causing the reagents within the bags to flow into the test chamber portion, and a low speed rotary motion of the rotor for reading test results.

22. The apparatus of claim 21 wherein said means for receiving and displaying is capable of performing kinetic and end point tests in any numbers at any of the cuvettes on said rotor.

23. The apparatus of claim 19 wherein said cuvettes each have flanges thereon, said flanges having said coding thereon and also serving as means for mounting said cuvette on said rotor.

24. Chemical test apparatus comprising:
    two pump sections of different dilution capability each having an aspirator dispenser hose;
    said apparatus having a receptacle therein which is shaped to permit insertion of a cuvette only when the cuvette is in a given orientation relative to said receptacle;
    a pair of switches mounted on said apparatus, one associated with one of said pump sections and the other associated with the other of said pump sections; each of said switches being positioned to be actuated by tab on the cuvette with the tab being oriented in accordance with the desired dilution of the liquid substance to be inserted into the cuvette.

25. The apparatus of claim 24 additionally comprising:
    a cuvette shaped for insertion into said receptacle only when the cuvette is in a given orientation relative to said receptacle.
    a tab mounted on said cuvette and oriented to actuate one or the other of said switches in accordance with the desired dilution of the liquid substance to be inserted into the cuvette.

* * * * *